United States Patent [19]

Updike et al.

[11] 4,421,854

[45] Dec. 20, 1983

[54] FERMENTATIVE PREPARATION OF L-LEUCINE

[75] Inventors: Mark H. Updike, Baltimore; Gary J. Calton, Elkridge, both of Md.

[73] Assignee: W. R. Grace & Co., New York, N.Y.

[21] Appl. No.: 388,901

[22] Filed: Jun. 16, 1982

[51] Int. Cl.³ .................... C12P 13/06; C12N 15/00; C12R 1/06
[52] U.S. Cl. .................................... 435/116; 435/172; 435/830
[58] Field of Search .................. 435/116, 172, 830

[56] References Cited

U.S. PATENT DOCUMENTS

| 3,865,690 | 2/1975 | Okumura et al. | 435/116 |
| 3,970,519 | 7/1976 | Tsuchida et al. | 435/116 |
| 4,237,228 | 12/1980 | Zhdanova et al. | 435/116 |

*Primary Examiner*—Lionel M. Shapiro
*Attorney, Agent, or Firm*—Jill H. Krafte

[57] ABSTRACT

L-leucine is prepared by cultivation of an analogue-resistant mutant of *Arthrobacter citreus* in an aqueous nutrient medium under aerobic conditions. The cultivation is preferably carried out at about 30° C. and at a pH of 5 to 0.8. L-leucine is recovered from the fermentation broth. In a preferred embodiment the mutant is further mutated, and the second mutant is similarly fermented to prepare L-leucine.

10 Claims, No Drawings

FERMENTATIVE PREPARATION OF L-LEUCINE

BACKGROUND OF THE INVENTION

Production of L-leucine, L-valine and other amino acids via fermentation has been the subject of considerable research. Numerous genera of microorganisms have been employed along with various amino acid analogues. U.S. Pat. No. 3,865,690 teaches production of L-leucine by culturing a strain of Brevibacterium or Corynebacterium made resistant to a leucine antagonist. U.S. Pat. No. 3,970,519 cultures strains of the same genera in the presence of various amino acids to produce L-leucine. From U.S. Pat. No. 3,893,888 it is known that L-valine can be produced from mutant strains of Brevibacterium resistant to α-amino-β-hydroxy valeric acid (AHV). U.S. Pat. No. 3,668,073 teaches preparation of L-leucine using a microorganism of the genus Corynebacterium in the presence of a "promoter" for isoleucine, methionine, phenylalamine or valine, e.g., azaleucine or AHV. Azaleucine has also been used as an analogue for producing L-leucine. See Wang et al, "Fermentation and Enzyme Technology," John Wiley and Sons, Inc., 1979, pages 18–20. U.S. Pat. No. 3,759,789 utilizes cultures of Arthrobacter alkanicus which are resistant to L-threonine. Precursors of L-leucine and L-isoleucine can be added to increase yields.

The following literature is relevant:
1. Araki, Kazumi, H. Ueda and S. Saigusa. Fermentative Production of L-Leucine with Auxotrophic Mutants of *Corynebacterium glutamicum*. Agr. Biol. Chem 38(3), 565–572 (1974).
2. Calvo, R. A., and J. M. Calvo. Lack of End-Product Inhibition and Repression on Leucine Synthesis in a Strain of *Salmonella typhimurium*. Science, 156, 1107–1109 (1967).
3. Kisumi, M., S. Komatsubara and I. Chibata. Leucine Accumulations by Isoleucine Revertants of *Serratia marcescens* Resistant to α-Aminobutyric Acid: Lack of Both Feedback Inhibition and Repression. J. Biochem., 73, 107–115 (1973).
4. Tsuchida, T., F. Yoshinaga, K. Kubota, H. Momose and S. Okumura. Cultural Conditions for L-Leucine Production by Strain No. 218, a Mutant of *Brevibacterium lactofermentum* 2256. Agr. Biol. Chem. 39(5), 1149–1153 (1975).
5. Tsuchida, T., and H. Momose, Genetic Changes of Regulatory Mechanisms Occurred in Leucine and Valine Producing Mutants Derived from *Brevibacterium lactofermentum* 2256. Agr. Biol. Chem. 39(11). 2193–2198 (1975).
6. Tsuchida, T., F. Yoshinaga, K. Kubota, H. Momose and S. Okumura. Production of L-Leucine by a Mutant of *Brevibacterium lactofermentum* 2256. Agr. Biol. Chem. 38(10), 1907–1911 (1974).
7. Freundlich, M. and J. M. Trela. (1969). Control of isoleucine, valine, and leucine biosynthesis. J. of Bacteriology, 101–106.
8. Izumi, Y., Y. Asano, Y. Tani and K., Ogata. (1977). Formation of valine and leucine by analog-resistant mutants of an obligate methylotroph, *Methylomonas aminofaciens*. J. Ferment. Technol., 55, 452–458.
9. Kisumi, M., S. Komatsubara and I. Chibata. (1977) Pathway for isoleucine formation from pyruvate by leucine biosynthetic enzymes in leucine-accumulating isoleucine revertants of *Serratia marcescens*. J. Biochem., 82, 95–103.
10. Kisumi, M., J. Kato, S. Komatsubara, I. Chibata. (1973). Production of isoleucine, valine and leucine by regulatory mutants of *Serratia marcescens*. "Genetics of Industrial Microorganisms—Bacteria".
11. Rogerson, A., and M. Freundlich. (1969). Control of isoleucine, valine and leucine biosynthesis. VIII. Mechanism of growth inhibition by leucine in relaxed and stringent strains of *Escherichia coli* K-12. Biochimica et Biophysica Acta, BRA 26302.

A general article on biosynthetic pathways for L-leucine as well as other amino acids has also been published. See:
12. Szentirmai, A. and I Horvath. (1976). Regulation of branched-chain amino acid biosynthesis. Acta Microbiol. Acad. Sci. Hung., 23, 137–149.
13. Umbarger, H. E. (1974) The elements involved in the multivalent regulation of the isoleucine and valine biosynthetic enzymes of the Enterobacteriaceae. Proceedings of the 1st. Intersectional Congress of IAMS, 1, Tokyo.
14. Umbarger, H. E. (1973). Genetic and physiological regulation of the isoleucine, valine and leucine biosynthetic enzymes of the Enterobacteriaceae. From "Genetics of Industrial Microorganisms."
15. Umbarger, H. E. (1978). Amino Acid Biosynthesis and Its Regulation. Ann. Rev. Biochem., 47, 533–606, 563.

DESCRIPTION OF THE INVENTION

The invention is a process for preparing L-leucine which comprises cultivating under aerobic conditions mutant strains of *Arthrobacter citreus* resistant to an analogue of L-leucine.

Wild strains of *Arthrobacter citreus* (e.g., ATCC 17775) selected for mutation are characterized by overproduction of glutamic acid. The biosynthetic pathway whereby microorganisms produce L-leucine is generally known. See for example Umbarger, "Amino Acid Biosynthesis and Its Regulation," Ann. Rev. Biochem. 1978. 47:563–565. As stated in this reference, the synthesis is believed to proceed through the following stages: pyruvate; α-acetolactate; α, β-dihydroxy isovalerate; α-ketoisovalerate; α-isopropylmalate; β-isopropylmalate; α-ketoisocaproate; L-leucine.

Certain analogues of the naturally occurring amino acids are suitable for isolating the mutant strains of this invention. These analogues are toxic to strains which do not overproduce L-leucine. Such analogues include α-amino-β-hydroxyvaleric acid; D-leucine; α-aminoisoamylsulfonic acid; norvaline; norleucine; methallylglycine; α-amino-β-chlorobutyric acid; valine; α-chloroleucine; isoleucine; β-hydroxynorleucine; β-hydroxyleucine; cyclopentene alanine; 3-cyclopentene-1-alanine; 2-amino-4-methylhexenoic acid; 5',5',5'-trifluoroleucine; 4-azaleucine.

The leucine analogue resistant mutant may be obtained by ultraviolet irradiation of a wild type strain of *Arthrobacter citreus* or by treating the wild strain with a mutagen, e.g., ethyl methane sulfonate, N-methyl-$N_1$-nitro-N-nitrosoguanidine, etc. Thereafter the strain can be cultured in the presence of the analogue to isolate the colonies which overproduce L-leucine.

A viable culture of an L-leucine-producing mutant strain of *Arthrobacter citreus* resistant to azaleucine (product of Example 1) has been deposited with the American Type Culture Collection, 12301 Park Lawn Drive, Rockville, Md. 20852, under No. ATCC 39103. Similarly a culture of the product of Example 2 has been deposited as ATCC 39106.

Fermentation of the isolated mutant strains of *Arthrobacter citreus* can be accomplished by shaking cultivation or submerged fermentation under aerobic conditions. The fermentation is carried out at 25° to 40° C. and at a pH of 5 to 8 (preferably 6.5 to 7.5). Calcium carbonate and/or ammonia may be employed for adjustment of the pH of the medium. Alternatively morpholino-sulfonic acid derivatives can be employed, e.g., see Example 1 below. The fermentation medium contains a source of carbon, a source of nitrogen and other elements. Suitable sources of carbon for the fermentation include fermentable sugars, protein hydrolysates and proteins. Examples of suitable sources of nitrogen are urea, ammonium salts of organic acids (e.g., ammonium acetate and ammonium oxalate) and ammonium salts of inorganic acids (e.g., ammonium sulfate, ammonium nitrate or ammonium chloride). The amounts of the carbon and nitrogen sources in the medium are from 0.001 to 20 w/v percent. Also, organic nutrients (e.g., corn steep liquor, peptone, yeast extracts, soybean extracts) and/or inorganic elements (e.g., potassium phosphate, magnesium sulfate, vitamins such as biotin and thiamine, and amino acids, e.g., valine) may be added to the medium. The fermentation is accomplished in 16 to 176 hours, and L-leucine is accumulated in the fermentation broth.

After the fermentation is completed, i.e., from 0.1 to 8.0 grams/liter of L-leucine is accumulated in the broth, cells and other solid culture components are removed from the fermentation broth by conventional procedures such as filtration or centrifugation. Known procedures may be employed in the recovery and/or purification of L-leucine from the filtrate or the supernatant solution. For instance, the filtered fermentation broth is treated with a strong cation exchange resin. Then the resin is eluted with a dilute alkaline solution such as aqueous ammonia. The eluates containing L-leucine are combined and concentrated. An alkanol such as methanol or ethanol is added to the concentrated solution. The precipitated crystals can be recrystallized from an aqueous alkanol such as aqueous methanol and aqueous ethanol to yield pure crystals of L-leucine.

The following examples illustrate without limiting the invention.

EXAMPLE 1

EMS Mutation and Resistance to Low Concentrations of Azaleucine

A fresh slant of *Arthrobacter citreus* (ATCC 17775) was washed with 0.1 M potassium phosphate buffer. The resulting cell suspension was decanted into a sterile tube to which ethyl methanesulfonate (EMS) was added in sufficient quantity to provide a 0.05 M concentration. The tube was incubated for 18 hours at 30° C. The cell suspensions were then centrifuged, the supernate was decanted, and the cells were resuspended in fresh buffer.

After two washings, the cells were used to inoculate a tube of the following medium (Medium E). A 10% inoculum was used.

| Medium E | |
|---|---|
| | Per liter deionized $H_2O$ |
| Glucose | 50 g |
| $NH_4Cl$ | 5 g |
| Urea | 5 g |
| $K_2HPO_4$ | 0.5 g |
| $KH_2PO_4$ | 0.5 g |
| $MgSO_4.7H_2O$ | 0.5 g |
| Biotin | 100 µg |
| Thiamine HCl | 1 mg |
| 3-(N—morpholino) propane sulfonic acid (i.e. "MOPS", Sigma Chemical Company) | 20.9 g |
| Trace element soln. (see below) | 1 ml |

The pH of the medium was adjusted to 7.0 with NaOH. The medium was autoclaved for 15 min. at 112° C. To prepare Medium E Agar add 15 g/l Agar Noble (Difco) to the Medium E solution.

The trace element solution was composed as follows:

| Trace Element Solution | |
|---|---|
| | Per liter of deionized water |
| $ZnSO_4.7H_2O$ | 8.8 gm |
| $FeSO_4.7H_2O$ | 10.0 gm |
| $CuSO_4.5H_2O$ | 60 mg |
| $Na_2B_4O_7.10H_2O$ | 88 mg |
| $Na_2Mo_2O_4.2H_2O$ | 53 mg |
| $MnSO_4.H_2O$ | 7.5 gm |
| $CoCl_2.6H_2O$ | 120 mg |
| $CaCl_2$ | 55 mg |

The pH of the trace element solution was adjusted to 2 with the $H_2SO_4$, and the solution was stored in a dark bottle at about 2°–0° C.

The cells were incubated for 17 hours at 30° C. in a gyrotary shaker at 300 RPM and were then plated out onto Medium E Agar (modified—only 2% glucose; the pH was adjusted to 7.8 before autoclaving) into which various levels (i.e. from 0.2 to 10 g/l) of azaleucine had been incorporated after autoclaving. The plates were incubated at 30° C. When colonies appeared (e.g., after about 2 to 4 days incubation) they were transferred to fresh Medium E Agar plates.

The azaleucine isolates were inoculated into tubes of Medium E and Isoleucine Medium 5, and incubated for three days at 30° C., 300 RPM.

| Isoleucine Medium 5 | |
|---|---|
| | Per liter D.I.[1] $H_2O$ |
| Glucose | 100 g |
| $(NH)_2SO_4$ | 50 g |
| $MgSO_4.7H_2O$ | 0.4 g |
| $CaCO_3$ | 50 g |
| $KH_2PO_4$ | 3 g |
| Bacto-soytone[2] | 0.6 g |
| Biotin | 100 µg |
| Thiamine HCl | 1 mg |
| Trace element solution | 1 ml |
| Adjust pH to 78 with NaOH. | |

[1]D.I. = deionized.
[1]An enzymatic hydrolysate of soybean meal sold by Difco Laboratories, Inc.

An isolate designated 17775-14, resistant to 4 g/l azaleucine, produced 4.56 g/l leucine in Isoleucine Medium 5, as assayed by high performance liquid chromatography (HPLC).

For analysis by HPLC, the amino acids are converted to their dansyl (see below) derivatives, then separated and quantitatively analyzed for each component by standard methods. The following procedure describes the derivatization of the amino acids for HPLC analysis.

PRINCIPLE

Dansyl chloride (1-dimethylaminonaphthalene-5-sulfonyl chloride) reacts with the amine group of amino acids. The dansyl derivatives can be separated by liquid chromatography and detected by ultraviolet absorption.

The reagents used in the foregoing HPLC are:
1. Buffer: Weigh 2.956 grams of lithium carbonate into a one liter flask and dilute to the mark with distilled water. Adjust the pH to 9.5 with concentrated hydrochloric acid.
2. Dansyl chloride solution: Weigh 75 mg of dansyl chloride into a 25 ml volumetric flask and dilute to the mark with acetonitrile.
3. Quencher: Weigh 5.0 grams of methylamine hydrochloride into a 250 ml volumetric flask and dilute to the mark with distilled water.
4. Acetic acid.
5. Amino acid standard H (Pierce Chemical Co., Cat. No. 20088).
6. Triethylamine.
7. Solvent mixture:
   877 ml distilled water
   100 ml methanol
   14 ml acetic acid
   20 ml tetrahydrofuran
   1.7 ml triethylamine

PROCEDURE

A. Preparation of Standards

1. Using a microsyringe, place 50, 100 and 200 µl of the Pierce amino acid standard in 5 ml volumetric flasks.
2. Place the 5 ml volumetric flasks in a vacuum desiccator and under vacuum, evaporate to dryness (usually requires overnight).
3. Pipet 2.0 ml buffer (Reagent No. 1 above) into each volumetric flask.
4. Pipet 1.0 ml dansyl chloride reagent (Reagent No. 2 above) into each volumetric flask.
5. Mix well and place in a 30° C. water bath for 30 minutes.
6. Add 100 µl quencher (Reagent No. 3) to each volumetric flask.
7. Mix well and allow to stand approximately 5 minutes.
8. Add 75 µl of acetic acid (Reagent No. 4) to each flask and mix.
9. Dilute to the marks with the solvent mixture (Reagent No. 7) and mix.
NOTE: Standards should be refrigerated until used.

B. Sample Preparation

NOTE: Refrigerant all samples received for analysis.
1. Place a 50 µl aliquot of each sample in a 5 ml volumetric flask.
2. Continue derivatization from Part A-3 above.

NOTE: Refrigerate derivatized samples until analyzed.

EXAMPLE 2

Second EMS Mutation and Resistance to Higher Concentrations of Azaleucine

The azaleucine resistant mutant, 17775-14, prepared in Example 1, was again submitted to ethyl methanesulfonate treatment, in the same manner as previously described.

After EMS mutation and overnight incubation at 30° C. in Medium E, the cells were washed once with 0.1 M phosphate buffer and plated out onto Medium E Agar containing azaleucine (added after autoclaving) in concentrations of from 4 to 20 g/l. The pH of the agars containing 12–20 g/l azaleucine had been adjusted to 9.6 with NaOH before autoclaving. The addition of 20 g/l azaleucine dropped the pH to 5.6 after autoclaving.

The plates were incubated for 3 to 7 days at 30° C. Resistant isolates were transferred to fresh Medium E plates, from which they were inoculated into tubes of Isoleucine Medium 5. After incubation at 30° C., 300 RPM for 3 days, the harvested broths were assayed by HPLC, as detailed in Example 1. An isolate designated 17775-14-7, resistant to 20 g/l azaleucine, was found to have a titer of 8.0 g/l leucine.

What is claimed is:

1. A process for preparing L-leucine which comprises cultivating under aerobic conditions a mutant strain of *Arthrobacter citreus* resistant to an analogue of L-leucine selected from the group consisting of α-amino-β-hydroxyvaleric acid; D-leucine; α-aminoisoamylsulfonic acid; norvaline; norleucine; methallylglycine; α-amino-β-chlorobutyric acid; valine; α-chloroleucine; isoleucine; β-hydroxynorleucine; β-hydroxyleucine; cyclopentene alanine; 3-cyclopentene-1-alanine; 2-amino-4-methylhexenoic acid; 5′,5′,5′trifluoroleucine, and 4-azaleucine, to yield a fermentation broth, accumulating from about 0.1 to about 8 grams/liter L-leucine in said fermentation broth, and recovering the accumulated L-leucine from said fermentation broth.

2. A process as in claim 1 wherein the mutant is *Arthrobacter citreus* ATCC 39103.

3. A process as in claim 1 wherein the fermentation is carried out at a temperature of from 25° to 40° C. for from 16 to 176 hours.

4. A process as in claim 1 wherein the pH of the fermentation media during cultivation is from 5 to 9.

5. A process as in claim 1 wherein the mutant is *Arthrobacter citreus* ATCC 39103 and fermentation is carried out at from 25° to 40° C. for 16 to 176 hours at a pH of from 5 to 8.

6. A process as in claim 1 wherein the mutant is *Arthrobacter citreus* ATCC 39106.

7. A process as in claim 3 wherein the mutant is *Arthrobacter citreus* ATCC 39106.

8. A process as in claim 4 wherein the mutant is *Arthrobacter citreus* ATCC 39016.

9. A process as in claim 3 wherein the mutant is *Arthrobacter citreus* ATCC 39103.

10. A process as in claim 4 wherein the mutant is *Arthrobacter citreus* ATCC 39103.

* * * * *

UNITED STATES PATENT AND TRADEMARK OFFICE
CERTIFICATE OF CORRECTION

PATENT NO. : 4,421,854
DATED : Dec. 20, 1983
INVENTOR(S) : Mark H. Updike and Gary J. Calton It is certified that error appears in the above-identified patent and that said Letters Patent is hereby corrected as shown below:

Claim 8, line 2, The ATCC No. designated should be --39106-- instead of "39016"

Signed and Sealed this

Sixth Day of March 1984

[SEAL]

Attest:

GERALD J. MOSSINGHOFF

Attesting Officer    Commissioner of Patents and Trademarks